United States Patent [19]
Cravatt et al.

[11] Patent Number: 5,478,728
[45] Date of Patent: Dec. 26, 1995

[54] PROCESS FOR ANTIBODY COMBINING SITE-CATALYZED SYN ELIMINATION IN THE FORMATION OF A CIS OLEFIN

[75] Inventors: Benjamin F. Cravatt, San Diego; Jon A. Ashley, Chula Visa; Kim D. Janda, San Diego; Dale L. Boger; Richard A. Lerner, both of La Jolla, all of Calif.

[73] Assignee: The Scripps Research Institute, La Jolla, Calif.

[21] Appl. No.: 296,323

[22] Filed: Aug. 25, 1994

[51] Int. Cl.⁶ .................. C12P 1/00; C12N 9/00
[52] U.S. Cl. .............. 435/41; 435/147; 435/166; 435/188.5; 435/240.27
[58] Field of Search ............ 435/188.5, 240.27, 435/166, 147, 41

[56] References Cited

U.S. PATENT DOCUMENTS 5,208,152  5/1993  Hilvert et al. .................. 435/119

OTHER PUBLICATIONS

Cravatt, B. F., et al. (1994) J. Am. Chem. Soc. 116, 6013–6014.
Boger, D. L., et al., (1994) J. Org. Chem. 59, 5078–5079.
Janda, K. D., et al. (1993) Science 259, 490–493.
Gouverneur, V. E., et al. (1993) Science 262, 204–208.

*Primary Examiner*—Charles L. Patterson, Jr.
*Attorney, Agent, or Firm*—Welsh & Katz, Ltd.

[57] ABSTRACT

A process is disclosed by which a substrate is catalytically converted to a cis olefin via a syn elimination reaction. The catalyst is a monoclonal antibody or paratope-containing molecule that binds to the substrate as well as to a bicyclo[2.2.1]heptane or bicylo[2.2.2]octane compound that is an analogue to the substrate having its bulky substituents in eclipsed positions. The chemical reaction is carried out in an aqueous medium. The catalyst molecules and hybridoma cells that secrete those molecules are also contemplated, as is a process for using cyclopentadiene or cyclohexadiene to prepare a hapten used to induce production of the catalyst molecules.

18 Claims, No Drawings

5,478,728

PROCESS FOR ANTIBODY COMBINING SITE-CATALYZED SYN ELIMINATION IN THE FORMATION OF A CIS OLEFIN

GOVERNMENTAL SUPPORT

This invention was made with government support under Contract No. GM 43858 by the National Institutes of Health. The government has certain rights in the invention.

DESCRIPTION

1. Technical Field

The present invention relates to antibodies, antigens and immunogens, and more particularly to a process that utilizes paratope-containing molecules that catalyze a syn elimination in the formation of a cis olefin.

2. Background of the Invention

Binding phenomena between ligands and receptors play many crucial roles in biological systems. Exemplary of such phenomena are the binding of oxygen molecules to deoxyhemoglobin to form oxyhemoglobin, and the binding of a substrate to an enzyme that acts upon it such as between a protein and a protease like trypsin (EC 3.4.21.4) or between (S)-2,3-epoxysqualene and lanosterol synthase (EC 5.4.99.7) in the formation of lanosterol. Still further examples of biological binding phenomena include the binding of an antigen to an antibody, and the binding of complement component C3 to the so-called CR1 receptor.

Many drugs and other therapeutic agents are also believed to be dependent upon binding phenomena. For example, opiates such as morphine are reported to bind to specific receptors in the brain. Opiate agonists and antagonists are reported to compete with drugs like morphine for those binding sites.

Ligands such as man-made drugs, like morphine and its derivatives, and those that are naturally present in biological systems such as endorphins and hormones bind to receptors that are naturally present in biological systems, and will be treated together herein. Such binding can lead to a number of the phenomena of biology, including particularly the hydrolysis of amide and ester bonds as where proteins are hydrolyzed into constituent polypeptides by an enzyme such as trypsin or papain, or where a fat is cleaved into glycerine and three carboxylic acids, respectively.

Slobin, *Biochemistry*, 5:2836–2844 (1966) reported preparing antibodies to a p-nitrocarbobenzoxy conjugate of bovine serum albumin. Those antibodies were thereafter used to hydrolyze p-nitrophenyl acetate and epsilon-aminocaproate esters. The reaction of the acetate ester was described by a second-order rate constant and was said to appear to be nonspecific. The second-order rate constant obtained using normal gamma globulin was said to be about equal to that of the specially prepared antibodies. The presence of the specially prepared antibodies, was said to inhibit the hydrolysis of the aminocaproate ester.

Kohnen and coworkers also reported attempts using antibodies to catalyze esterolysis. The antibodies utilized by this group were, in each instance, raised to a portion of the ultimately utilized substrate molecule that did not contain the bond to be hydrolyzed.

In their initial work [*FEBS Letters*, 100:137– 140 (1979) and *Biochim. Biophys. Acta*, 629:328–337 (1980)] antisteroid antibodies were used to hydrolyze 7-umbelliferone (7-hydroxycoumerin) esters of a carboxyethyl thioether of asteroid. In each instance, an increase in hydrolyric rate was observed as compared to background or to a rate obtained with normal IgG. In both instances, turnover numbers were low (about one mole of substrates per mole of antibody per minute, or less), and the reaction rates declined with time, reaching a plateau with saturation of the antibody. That slow down in rate was attributed to an irreversible binding of the steroidal acid product to the antibody.

Kohen et al. also reported hydrolysis of 7-[-N-(2,4-dinitrophenyl)-6-aminohexanoyl]-coumerin using monoclonal antibodies raised to the dinitrophenyl portions of that substrate molecule [*FEBS Letters*, 111:427–431 (1980)]. Here, a rate increase over background was also reported, but the reaction was said to be stoichiometric rather than catalytic. A decrease in rate that approached zero was reported as saturation of the antibody was reached. Again, the decrease was attributed to product inhibition caused by binding of the product acid to the antibody since some of the initial hydrolysis activity could be regenerated by chromatography of an antibody-substrate-product mixture.

When strong antibody binding is directed to stable states of substrate molecules, the slow rate of dissociation of the complex impedes catalysis. Such is thought to be the situation for the results reported by Kohnen and coworkers.

The above constructs, though interesting, are severely limited by the failure to address the mechanism of binding energy utilization that is essential to enzymes [W. P. Jencks, *Adv. Enzymol.*, 43, 219 (1975)].

Those deficiencies can be redressed by using a transition state analogue as the hapten to elicit the desired antibodies. This hapten (also referred to herein as an "analogue ligand") can assume the role of an inhibitor in the catalytic system.

Thus, immunological binding can be used to divert binding interactions to catalytic processes. For example, it was suggested that use of an antibody to a haptenic group that resembles the transition state of a given reaction should cause an acceleration in substrate reaction by forcing substrates to resemble the transition state. Jencks, W. P., *Catalysis in Chemistry and Enzymology*, page 288 (McGraw-Hill, New York 1969). Notwithstanding that broad suggestion, specific transition state haptens were not suggested, nor were specific reactions suggested in which the concept might be tested.

Hydrolysis of amide and ester bonds is thought by presently accepted chemical theory to proceed in aqueous media by a reaction at the carbonyl carbon atom to form a transition state that contains a tetrahedral carbon atom bonded to (a) a carbon atom of the acid portion of the amide or ester, (b) two oxygen atoms, one being from the carbonyl group and the other from a hydroxyl ion or water molecule of the medium, and (c) the oxygen atom of the alcohol portion of an ester or the nitrogen atom of the amine portion of an amide. Transition states of such reactions are useful mental constructs that by definition, cannot be isolated, as compared to intermediates, which are isolatable.

Although the above hydrolytic transition states cannot be isolated, a large amount of scientific literature has been devoted to the subject. Some of that literature is discussed hereinafter.

Whereas the before-described transition state for amide and ester hydrolyses is believed to be well understood, the parameters of the topology, e.g., size, shape and charge, of receptor binding sites in which particular amides, such as proteins, or esters, such as fats, react through those transition states is not as well understood. It would therefore be beneficial if the topology of a plurality of binding sites were known so that the interactions of the ligands that bind in those sites could be studied. Unfortunately, the topology of receptor binding sites in the well-studied field of biological hydrolyses is generally unknown, except for a relatively small number of enzymes whose X-ray crystal structures have been determined.

This lack of knowledge of binding site topology stems in part from a lack of knowledge of even the location in cells of many binding sites of receptors. In addition, for those receptor binding sites whose location is known, the chemical identity, i.e., protein and carbohydrate composition, of the binding site is generally unknown. Thus, the investigator is generally stymied in seeking to understand the topological requirements of receptor binding sites and therefore in seeking to construct therapeutic agents that can fulfill those requirements.

Investigators must therefore screen potential therapeutic agents in animal or cell culture studies to ascertain whether a potential therapeutic agent may be useful. Such systems, while useful, are expensive and time-consuming to use.

Even where the topology and chemical reactivity of a hydrolytic receptor such as an enzyme are known, enzymes such as hydrolyric proteases typically cleave their substrates, polypeptide chains, adjacent to a particular amino acid residue that may occur several times in the polypeptide chain of the protein. While such relatively random cleavage can be useful in obtaining a polypeptide map of the protein, that relatively random cleavage is not as useful where particular amino acid residue sequences are desired to be produced.

Recently, Lerner, Tramontano and Janda [*Science*, 234, 1566 (1986)] reported monoclonal antibodies to hydrolyze esters in U.S. Pat. No. 4,656,567. Pollack, Jacobs and Schultz [*Science*, 234, 1570 (1986)] reported a myeloma protein denominated MOPC167 [Leon et al., *Biochem.*, 10, 1424 (1971)] that catalyzes the hydrolysis of a carbonate.

In the two Lerner and Tramontano disclosures, the antibodies were raised to a phosphonate that was synthesized to represent a stable analogue of the tetrahedral hydrolyric transition state of the carboxylic acid ester or carbonate ester. The Pollack et al. antibody principally discussed was a myeloma protein that happened to bind to a phosphonate that was structurally analogous to the carbonate analogue hydrolyzed. Thus, in the Lerner and Tramontano et al. work, the substrate to be hydrolyzed was preselected, with the immunizing analogue and hydrolyric antibodies being synthesized in accordance with the desired product. Pollack et al. designed the substrate to be hydrolyzed once they knew the specificity of the myeloma protein. Pollack et al. also reported (above) the existence of a catalytic antibody, substrated and analogue substrate system for carbonate hydrolysis similar in concept to that of Lerner et al. Work relating to that system is reported in Jacobs et al., *J. Am. Chem Soc.*, 109, 2174 (1987).

U.S. Pat. No. 4,888,281 (Schochetman et al.) discusses the possible use of antibodies as catalysts, and presents data relating to the use of polyclonal serum in hydrolyzing o-nitrophenyl-beta-D-galactoside. The antibodies useful in that patent are said to be inducible by a reactant, a reaction intermediate or to an analogue of the reactant, product or reaction intermediate. The term "analogue" is there defined to encompass isomers, homologs or other compounds sufficiently resembling the reactant in terms of chemical structure that an antibody raised to an analogue can participate in an immunological reaction with the reactant but will not necessarily catalyze a reaction of the analogue.

The data provided in that specification only indicate that some cleavage of the substrate (reactant) galactoside occurred over an eighteen hour time period using a relatively concentrated antibody preparation (1:10 and 1:20 dilutions). Although catalysis was alleged, catalytic activity was not shown since no turnover of the allegedly catalytic antibody was shown, nor was there an indication of the percentage of substrate galactoside cleaved. The patent did indicate that beta-D-galactosidase cleaved about ten times as much substrate as did the polyclonal antibodies, presuming linearity of absorbance at the unnamed concentration of substrate studied.

From the data presented in that patent, it is possible that a nucleophilic replacement of the o-nitrophenyl group occurred by a terminal amino group of a lysine residue of the antibody preparation used. Thus, the observed absorbance could have been due to formation of epsilon-amino lysinyl o-nitrophenyl aniline or to the formation of an epsilon-amino-lysinyl galactoside and o-nitrophenol, either of which occurrences would not be catalytic since the antibody was consumed, rather than turning over.

U.S. Pat. No. 4,792,446 (Kim et al.) discusses the possible use of antibody catalysts in the synthesis of chiral molecules. However, such syntheses were neither described nor disclosed in that patent.

In more recent work, bimolecular amide formation catalyzed by antibody molecules has been disclosed [Benkovic et al., *Proc. Natl. Acad. Sci. USA*, 85:5355 (1988)], as has an antibody-catalyzed Claisen rearrangement [Jackson et al., *J. Am. Chem. Soc.*, 110:4841 (1988)]. None of that work, nor the previously discussed work, has contemplated the use of antibodies to catalyze any reaction in a stereospecific manner.

Stereospecificity was shown in an antibody-catalyzed lactone-forming reaction [Napper et al., *Science*, 237:1041 (1987)] and in an antibody-catalyzed Claisen reaction [Hilvert et al., *Proc. Natl. Acad. Sci. USA*, 85:4955 (1988)].

U.S. Pat. No. 5,208,152 describes use of catalytic antibodies to catalyze a Diels-Alder (4+2) cycloaddition reaction. That catalyst binds to two substrate molecules, a conjugated diene and dienophile that react to form an intermediate that itself decomposes to expel a leaving group and form a 5- or 6-membered ring compound.

Antibody molecules were also reported as useful in catalyzing a disfavored cyclization of an epoxyalcohol to form a hydroxytetrahydropyran in Janda et al., *Science*, 259:490–493 (1993). In the latter disclosure, the catalytic antibodies were raised to a 6-membered cyclic N-oxide hapten to presumptively induce complementary charges in the antibody binding pocket while using the binding energy from substrate binding to organize the reaction geometry to favor the desired, disfavored 6-membered ring product over the usually obtained 5-membered ring product in that acid-catalyzed reaction. That acid-catalyzed reaction utilized a regioselective 6-endo-tet ring opening of an epoxide by an internal nucleophilic oxygen atom to form the ring.

Gouverneur et al., *Science*, 262:204–208 (1993) reported another antibody-catalyzed Diels-Alder cycloaddition reaction. There, two monoclonal antibodies were described, one of which catalyzed formation of the energetically favored endo product and the other of which catalyzed the energetically disfavored exo product. When the cycloaddition reaction was carried out in the absence of catalyst, the ratio of endo to exo product was about 85:15, whereas greater than 98 percent enantioselectivey was observed when either antibody was used as catalyst.

Exemplary embodiments of the present invention were partly disclosed in Cravatt et al., *J. Am. Chem. Soc.*, 116:6013–6014 (1994) by the inventors and their co-workers.

SUMMARY OF THE INVENTION

The present invention contemplates use of a receptor molecule that is a monoclonal antibody molecule or a molecule that contains an antibody combining site or paratope to catalyze the formation of a cis olefin from an open chain (acyclic) substrate ligand via an energetically disfavored syn elimination. This process comprises the steps of:

(a) admixing in an aqueous medium at a pH value of about 7 to about 10
  (i) an acyclic substrate ligand of the formula I to form a reaction mixture

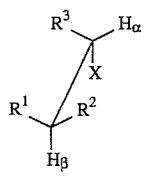

I wherein $R^1$ is a substituent containing a five- or six-membered ring or a chain of atoms long enough to fold to approximate the structure of a five- or six-membered ring;

$R^2$ is a substituent group other than hydrogen having a steric bulk that is less than that of $R^1$; and the sum of the Hammett $\sigma_m$ values of $R^1$ and $R^2$ is about +0.3 to about +0.8;

$R^3$ is a substituent containing a five- or six-membered ring or a chain of atoms long enough to fold to approximate the structure of a five- or six-membered ring, and has a Hammett $\sigma_p$ value of about zero or less;

X is a leaving group; and $H_\alpha$ and $H_\beta$ are hydrogens bonded to carbon atoms $\alpha$ and $\beta$ to X, respectively; and (ii) a catalytically effective amount of monoclonal antibodies or paratope-containing portions that bind to said substrate and also bind to a bicyclic immunogen having the structure of formula III

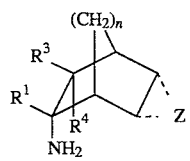

III wherein
(a) $R^1$ and $R^3$ are as defined above;
  $R^4$ is a hydrogen or a substituent of about the same size as X;
  n is 1 or 2; and
  Z is a carboxyl-terminated haptenic linking group for bonding the analogue ligand to an immunogenic carrier, Z being bonded to one or the other of the two carbons of formula III to which Z is linked by dotted lines; and (b) maintaining that reaction mixture under biological reaction conditions for a time period sufficient for the substrate ligand to be converted to a corresponding cis olefin of formula II

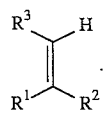

II

Also contemplated are hybridoma cells that secrete a monoclonal antibody that catalyzes an above-described syn elimination reaction and the monoclonal antibody catalyst molecules or paratope-containing portions secreted by such hydribdoma cells are also contemplated.

Yet another aspect of the invention is a process for using cyclopentadiene or cyclohexadiene to form (prepare) a hapten molecule containing eclipsed substituent groups useful herein for inducing production of paratope-containing molecules that catalyze the syn elimination of an acyclic substrate ligand of formula I

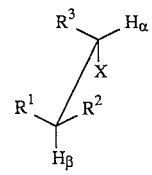

I wherein $R^1$ is a substituent containing a five- or six-membered ring or a chain of atoms long enough to fold to approximate the structure of a five- or six-membered ring;

$R^2$ is a substituent group other than hydrogen having a steric bulk that is less than that of $R^1$; and the sum of the Hammett $\sigma_m$ values of $R^1$ and $R^2$ is about +0.3 to about +0.8;

$R^3$ is a substituent containing a five- or six-membered ring or a chain of atoms long enough to approximate the structure of a five- or six-membered ring, and has a Hammett $\sigma_p$ value of about zero or less; and X is a leaving group.

This process comprises the steps of:

(a) reacting cyclopentadiene or cyclohexadiene in a Diels-Alder reaction with a cis nitro-olefin of formula IV

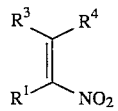

IV wherein
  $R^1$ and $R^3$ are defined above; and
  $R^4$ is a hydrogen or a substituent of about the same size as X, to form a compound of formula V

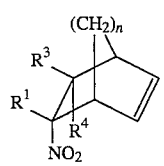

V (b) reducing the ethylenic double bond of a compound of formula V with a borane reductant and oxidizing the product of that reduction to form an alcohol of formula VI

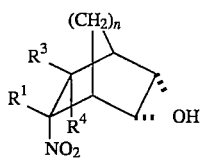

wherein the depicted hydroxyl group is bonded to one or the other of the two carbons of formula VI to which it is linked by dotted lines;

(c) reacting an alcohol of formula VI with a diacid or diacid precursor to form a compound of formula VII

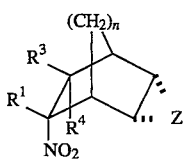

wherein Z is a carboxyl-terminated haptenic linking group, and is bonded to one or the other of the two carbon atoms of a compound of formula VII to which Z is linked by dotted lines;

(d) reducing the nitro group of a compound of formula VII to form the corresponding amine compound of formula III;

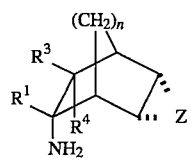

wherein Z is a carboxyl-terminated haptenic linking group, and is bonded to one or the other of the two carbons of formula III to which Z is linked by dotted lines; and recovering the compound of formula III.

The word "cis" is used herein as it is normally used in organic chemistry to mean that like substituent groups are on the same side of the double bond. The word "trans" is similarly used to mean that the like groups are on opposite sides of the double bond. Where the like groups are not identical, the like substituents are those most similar in size, and more particularly, the cis substituents are $R^1$ and $R^3$ as discussed hereinafter. Cis substituents thus are in the more recently used Z relation, whereas trans substituents are in the E relation.

The present invention provides several benefits and advantages.

One benefit of the invention is that desired cis (Z) olefin molecules can be formed from precursor molecules that heretofore could only be used to form the corresponding trans (E) isomers.

An advantage of the reaction is that the desired syn elimination product can be prepared in high isomeric purity.

Still further benefits and advantages of the present invention will be apparent to those skilled in the art from the discussion that follows.

DETAILED DESCRIPTION OF THE INVENTION

I. Introduction

The present invention relates to molecules collectively referred to as receptors that are antibodies or paratope-containing (antibody combining site-containing) portions induced by an analogue of an acyclic or open chain substrate whose substituent groups are in an energetically disfavored eclipsed configuration. The analogue ligand mimics the stereochemistry and conformation of the unisolatable transition state in the reaction pathway for the syn elimination of that substrate. The receptor molecules (antibodies and antibody combining sites; i.e., paratope-containing molecules) that bind to the analogue ligand and to the substrate are thought to stabilize the transition state on the reaction pathway between a substrate reactant ligand and olefin product by configurationally orienting the bound substrate into a desired energetically disfavored, eclipsed configuration from which a syn rather than anti-elimination occurs. The product is released from the catalyst after formation.

The cis olefin products of the reaction are useful monomers for polymerization reactions. In addition, these olefins can be used to react with halogens such as $Cl_2$ or $Br_2$ as where a halogenation reaction is run and excess, remaining halogen is consumed by a produced cis olefin prior to work-up of the reaction mixture to obtain a desired halogenation product.

Antibodies and enzymes are both proteins whose function depends on their ability to bind specific target molecules. Enzymatic reactions differ from immunological reactions in that in an enzymatic reaction the binding of the enzyme to its substrate typically leads to chemical catalysis, whereas a non-catalytic complex is the usual result of antibody-antigen binding.

Enzymes are believed to catalyze reactions such as the hydrolysis of proteins by combining with the protein to stabilize the transition state of the hydrolysis or other reaction. It is generally believed that the rate of an enzymatic reaction is increased relative to the rate of a non-enzymatic reaction because of the ability of the enzyme to stabilize the transition state of the reaction; i.e., to reduce the free energy of the transition state, and thus, the free energy of activation, of the reaction [Jencks, W. P., Adv. Enzymology, 43, 219 (1975) and Pauling, L., Amer. Scientist, 36, 58 (1948)]. Support for this theory comes from the observation that substances that are thought to model the presumed transition states are often strongly bound to the enzymes as competitive inhibitors. Leinhard, G., Science, 180, 149 (1973) and Wolfenden, R., Acc. Chem. Res., 5, 10 (1972). It is further thought that the enzyme accomplishes this lowering of the reaction free energy by binding the transition state geometry of the reactant more strongly than it binds to the corresponding substrate(s) or product(s).

This means that the intrinsic binding energy of the enzyme is much greater than can be measured from the binding of substrates or products. Essentially, the binding energy of the enzyme is utilized to perform the chemical reaction [Jencks, W. P., XVII International Solvay Conference (November 1983)].

The converse proposition is that an antibody that is prepared to optimally bind a suitable analogue of a transition state would function as a catalyst. The demonstration of this result by Lerner and co-workers and Schultz and co-workers in the previously cited disclosures completes the correlation of enzyme function and antibody structure and provides a useful approach to devising artificial enzymes.

The basic idea behind immunological catalysis described herein contemplates the use of analogue ligands in the preparation of antibodies of predetermined specificity that specifically and preferentially bind to and thereby stabilize the transition state for syn elimination upon binding to the specified substrate reactant ligand. An analogue ligand simulates the conformation of a high energy transition state in a cis olefin-forming reaction to induce the production of antibodies having the ability to bind related substrates and stabilize their cis olefin-forming reactions.

Such preferential binding and stabilization results in a reduction in the activation energy for the elimination reaction, thus meeting a criterion for catalysis. Antibodies that display this property can be obtained by immunization with a synthetic analogue that resembles the size and bonding characteristics of a substrate reactant ligand undergoing syn elimination; i.e., by immunization with transition state analogue of the particular syn elimination reaction.

In addition, a receptor molecule of the present invention also releases the formed product without itself reacting in a catalyzed process, referred to as turnover so that one antibody molecule can form several product molecules in a given time period. Such turnover meets another criterion for catalysis.

The mechanism by which an antibody catalyzes syn elimination and olefin formation of a bound reactant ligand can be thought of in terms of an "induced fit" model. As the loosely bound substrate distorts or rearranges to conform to the binding geometry induced upon it by the antibody combining site, the bulky substituents at the α- and β-carbons (the $R^1$ and $R^3$ substituent groups discussed hereinafter) change from their low energy, staggered conformation to a high energy, eclipsed configuration with the α-carbon leaving group (X) and β-carbon proton ($H_\beta$) having a synperiplanar conformation; i.e., the leaving group, X, and $H_\beta$ have a dihedral angle of zero degrees.

The term "receptor" is used herein to mean a molecule that binds to a reactant ligand, inhibitor ligand, or analogue ligand. The receptor molecules of the present invention are antibodies or other paratope-containing polyamide portions of an antibody.

Paratope-containing portions (antibody combining sites or idiotypes) of antibodies are those portions of antibody molecules that include the idiotype, and bind to the ligand or analogue ligand. Such portions include the Fab, Fab', Fv and F(ab')$_2$ fragments prepared from antibodies by well-known enzymatic cleavage techniques. See for example, U.S. Pat. No. 4,342,566 to Theofilopoulos and Dixon, generally, and specifically, Pollack et al., [*Science*, 234, 1570 (1987)] who reported accelerated hydrolyric rates for Fab fragments were the same as those of the native immunoglobulin. Inasmuch as the antibodies from which paratope-containing positions are obtained are described as raised against or induced by immunogens, paratope-containing (antibody combining site-containing) receptors can also be discussed as being "raised" or "induced" with the understanding that a cleavage step is typically required to obtain only an idiotype-containing polyamide from an antibody. Intact antibodies are preferred, however, and are utilized as illustrative of the receptor molecules of this invention.

The receptors useful in the present invention are monoclonal antibodies. A "monoclonal antibody" is a receptor produced by clones of a single cell called a hybridoma that secretes but one kind of receptor molecule. The hybridoma cell is fused from an antibody-producing cell and a myeloma cell or other self-perpetuating cell line.

Techniques for preparing the monoclonal antibodies of the present invention are well known. Such receptors were first described by Kohler and Milsrein, *Nature*, 256, 495 (1975), which is incorporated herein by reference. Monoclonal antibodies are typically obtained from hybridoma tissue cultures or from ascites fluid obtained from mammals into which the hybridoma tissue was introduced. Both methods are described herein.

A "ligand" is defined herein as a molecule that immunoreacts with or binds to a useful receptor molecule antibody combining site. Two types of ligand are contemplated herein. A first is termed an analogue ligand and is used as an immunogen (hapten) when bonded to an appropriate immunogenic carrier to induce preparation of receptor molecules and as an inhibitor of the receptor molecule-catalyzed reaction when present without the carrier. The analogue ligand is inert to undergoing the catalyzed reaction. The second ligand is referred to as the reactant ligand, substrate ligand, substrate or similar phrase and is an acyclic molecule that undergoes the catalyzed elimination reaction. The substrate and analogue ligands are structurally analogous.

Short polypeptide chains can induce the production of antibodies that recognize and bind to a homologous protein at a predetermined specific site. The present invention carries the earlier work with polypeptides a major step forward. Here, the antibodies (receptors) are induced by an immunizing haptenic first molecule (the analogue ligand), and recognize and bind not only to that first molecule, but also to a second, structurally analogous molecule (the substrate reactant ligand).

In binding that second molecule, the receptor catalyzes elimination in a reaction (which as demonstrated herein is catalytic) of preselected atoms to form a cis olefin compound. Inhibitor ligands that resemble the structure of an analogue ligand or a reactant ligand are also bound by receptor molecules and do not undergo a reaction catalyzed by the receptor.

Consequently, by synthesis of a relatively small, immunizing haptenic analogue ligand, one can induce the production of receptor molecules that recognize, bind to and catalyze elimination in another molecule that can contain a plurality of sites for elimination. Thus, receptor molecules can be prepared that catalyze elimination between selected, predetermined carbon atoms of a preselected compound to yield a cis olefin product.

The implication of this result is that one can confer the activity of hitherto known or unknown dehydrase enzymes to immunoglobulins. Furthermore, the activity of the antibody combining site can be directed to any predetermined site at will by substituent group placement in the haptenic analogue ligand used for immunization.

II. Transition State of Epoxidation and Hapten (Analogue Ligand) Design

Design of the analogue ligand flows backward from the structure of the product to be formed through the transition state for bond formation to be mimicked, to the substrate and then to the analogue ligand. The general reaction type of interest here will be discussed below, followed by a brief discussion of the products, and then more detailed discussions of the substrate and analogue ligands to which a monoclonal catalytic molecule binds, as the structures of the substrate and analogue ligands to which the catalyst binds define the catalyst used in the process.

The reaction contemplated here is the antibody paratope-catalyzed syn elimination of a particularly substituted acyclic substrate ligand to form the corresponding cis olefin. The corresponding cis olefin product formed depends mostly upon the substrate molecule that includes two five- or six-membered rings, or atom chains that can fold to approximate the cyclic structure of such rings.

A contemplated substrate ligand is acyclic, at least as to the carbon atoms between which the elimination takes place. That is, the two carbon atoms between which the elimination takes place are not themselves in a ring.

Those two carbon atoms are referred to as the α-carbon and the β-carbon. The nucleofuge or leaving group, X, is bonded to the α-carbon, whereas the hydrogen that is removed is bonded to the β-carbon and that hydrogen is referred to herein as $H_\beta$. The α-carbon also contains a hydrogen atom, and that hydrogen is designated $H_\alpha$.

An exemplary substrate contains two substituents, other than hydrogen, bonded to the β-carbon. Those substituents are referred to as $R^1$ and $R^2$. The α-carbon contains the nucleofuge (X), a hydrogen ($H_\alpha$) and another substituent that is other than hydrogen and is designated $R^3$.

An exemplary substrate ligand can assume the configuration for $R^1$, $R^2$, $H_\beta$, $H_\alpha$, X and $R^3$ that is shown below in formula I.

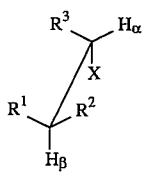

More specifically in formula I:

$R^1$ is a substituent containing a five- or six-membered ring or a chain of atoms long enough to fold to approximate the structure of a five- or six-membered ring. Actual ring compounds are preferred, and it is more preferred that the ring structure contain ethylenic unsaturation, most preferably aromatic unsaturation.

Exemplary ring-containing substituents include phenyl, 1- or 2-naphthyl, cyclohexyl, cyclohexenyl, cyclopentyl, 2-cyclopentenyl, 2-, 3- or 4-pyridyl, 2- or 3-furanyl and the like. An acyl ring-containing structure is more preferred, and an aromatic acyl ring-containing substituent is most preferred. Exemplary acyl ring-containing substituents include benzoyl, 1- or 2-naphthoyl, cyclohexylcarbonyl, cyclopentylcarbonyl, 2-, 3- or 4-pryidinoyl, cyclohex-2-enylcarbonyl and the like. An acyclic chain of atoms that can fold to approximate the structure of a five- or six-membered ring includes pentyl, pent-3-enyl [—CH$_2$)$_2$—CH=CH—CH$_3$], hexyl, hexa-2,4-dienyl (—CH$_2$CH=CH—CH=CH—CH$_3$), heptyl, octyl, nonyl, decyl and their mono- and di-ethylenically unsaturated groups and ethoxyethyl, as well as their corresponding acyl analogues such as pentanoyl, penta-3-enoyl, hexanoyl and the like. Thus, $R^1$ can contain a chain containing up to about 10 atoms.

A ring compound can also be substituted with a $C_1$–$C_4$ hydrocarbyl group such as methyl, ethyl, iso-propyl, sec-butyl, allyl, but-3-enyl and the like, as well as a halo group such as fluoro, chloro, bromo or iodo groups, a nitro group, a $C_1$–$C_4$ hydrocarbyloxy group; i.e., an ether of a $C_1$–$C_4$ hydrocarbyl group, a cyano group and a $C_1$–$C_4$ acyl group such as formyl, acetyl, propionyl and iso-butyryl. A chain of atoms long enough to fold to approximate the structure of a five- or six-membered ring can also be similarly substituted. A benzoyl group is a particularly preferred $R^1$ substituent.

Substituent $R^2$ is a group other than hydrogen having a steric bulk or volume that is less than that of $R^1$. The phrase "other than hydrogen" or a similar phrase is meant to include deuterium and tritium whenever it is used herein. Except as discussed below, $R^2$ can thus be any group other than hydrogen, deuterium or tritium whose steric bulk; i.e., average substituent volume, is less than that of hydrogen.

Exemplary $R^2$ groups include hydrocarbyl groups, cyano, nitro, nitro-substituted $C_1$–$C_3$ alkyl such as nitromethyl, halo-substituted $C_1$–$C_3$ alkyl groups such as trifluoromethyl, 2,2-dichloroethyl and the like, and $C_2$–$C_3$ acyl groups.

Steric bulk is quantified using $E_s$ values as are discussed in J. March, *Advanced Organic Chemistry*, 4th ed., John Wiley & Sons, New York (1992) page 285, and the citations therein. Steric bulk or volume can also be suitably approximated by use of commonly available molecular models and computer programs.

The second limitation on an $R^2$ substituent and also an $R^1$ substituent is that the sum of the Hammett $\sigma_m$ values of $R^1$ and $R^2$ is about +0.3 to about +0.8, and more preferably, about +0.4 to about +0.7. Tables of Hammett $\sigma_m$ (sigma for meta substituents) values can be found in J. Hine, *Physical organic Chemistry*, 2nd ed., McGraw-Hill Book Co., Inc., New York (1962) page 87; and in J. March, *Advanced Organic Chemistry*, 4th ed., John Wiley & Sons, New York (1992) page 280; as well as in the chemical literature.

The basis for this limitation is that the $R^1$ and $R^2$ substituents govern the acidity of $H_\beta$ and the sum of the Hammett $\sigma_m$ values correlate to the approximate $pK_a$ of $H_\beta$. Thus, for the desired elimination to occur, $H_\beta$ must be sufficiently acidic to be removed by a base present in the reaction medium that here is an aqueous medium that contains a proteinaceous catalyst that is itself susceptible to base-catalyzed hydrolysis and decomposition. On the other hand, $H_\beta$ must not be so acidic that a spontaneous reaction predominates, because such a spontaneous reaction can follow an anti-elimination to form the undesired transolefin via the energetically more favored uncatalyzed pathway.

A $pK_a$ value of about 15–19 for $H_\beta$ is sufficiently acidic for a desired syn elimination reaction to occur with little, if any anti-elimination when the receptor-catalyzed reaction is carried out in an aqueous medium at a pH value of about 7 to about 10. Use of $R^1$ and $R^2$ groups having a sum of Hammett $\sigma_m$ values nearer to about +0.8 is useful at lower pH values, whereas a sum nearer to about +0.3 is useful at higher pH values.

It is also to be understood that $pK_a$ values measured in aqueous media can vary and that Hammett $\sigma_m$ values were developed for systems other than those contemplated here. In addition, some substituent groups such as methylsulfonyl have large Hammett $\sigma_m$ values, which when summed, do not correlate well with $pK_a$ values. Thus, although use of the sum of Hammett $\sigma_m$ values is not absolutely predictive of the value of $H_\beta$, use of such sums provides the worker of ordinary skill with a ready starting place for design of a useful substrate from which little, if any, further experimentation is required. In addition, the skilled worker can plot summed Hammett $\sigma_m$ values for compounds of known acidity to assist in determining an appropriate substrate molecule.

Turning now to the α-carbon and its substituents, one of those substituents is a hydrogen designated $H_\alpha$. Another substituent is $R^3$ that contains a five- or a six-membered ring or a chain of atoms long enough to fold to approximate the structure of a five- or six-membered ring, and is thus other than hydrogen. The $R^3$ substituent also has a Hammett $\sigma_p$ (sigma for para substituent) value of about zero or less.

An $R^3$ substituent group can thus be one of the $R^1$ ring structures or chains discussed previously for $R^3$ that has an appropriate Hammett $\sigma_m$ value. It is noted that a phenyl group has a $\sigma_p$ value of about −0.01, and a p-methoxyphenyl group has a $\sigma_p$ of about −0.10, whereas a p-nitrophenyl group has a $\sigma_p$ value of +0.26. Thus, a phenyl group used as an $R^3$ substituent can have a $C_1$–$C_4$ alkyl ether substituent, but not a nitro substituent. An $R^3$ substituent with a Hammett $\sigma_p$ value of about zero or less helps stabilize the relative positive charge built-up on the α-carbon as the leaving group departs. Phenyl is a particularly preferred $R^3$ group.

The nucleofuge or leaving group, X, includes those normally utilized in an elimination reaction. Exemplary leaving groups include the halo (fluoro, chloro, bromo and iodo) substituents, the sulfonates such as methanesulfonate, toluenesulfonate and trifluoromethanesulfonate, and a tri-$C_1$-$C_4$ alkyl ammonium compound such as trimethylammonium. Further exemplary leaving groups are found in March, supra, at page 1005. It is preferred that the nucleofuge be relatively small, so that alkyl groups are $C_1$-$C_4$, with methyl being preferred. Fluoro is a particularly preferred leaving group.

One basis for the requirement of the substrate ligand having two five- or six-membered rings is to assist in binding of the substrate ligand by the binding site of antibody catalyst. An antibody combining site (paratope or binding pocket) is usually reported to be able to accommodate about 5–7 amino acid residues. A seven residue chain includes a chain of about 25 atoms including the N-terminal amino group (—$NH_2$) and C-terminal carboxyl group (—OH). Side chains must also be accommodated within the paratope.

That paratopic size is also about the size of a squalene oxide molecule (30 carbons) from which the steroid lanosterol is formed. In addition, Arevalo et al., *Nature*, 365:859–863 (1993) recently reported that the combining site of a non-catalytic monoclonal anti-progesterone antibody Fab' fragment designated DB3 could accommodate 81–91 percent of each of five steroidal molecules. That paper also noted that the steroidal D ring was embedded in a hydrophobic cavity at the bottom of the binding pocket of that paratope.

Extending the induced fit model for antibody binding to an olefin-forming elimination reaction, the size of the substrate here is limited so that substantially all of the substrate; i.e., 80–100 percent, and particularly the olefin-forming portion with its two rings or chains that can each fold to approximate the size and shape of a ring, can be within the catalytic paratope. Such a size limitation can thereby utilize the binding energy of the antibody-substrate binding interaction to overcome otherwise contrary entropic and/or enthalpic effects present when forming an olefin by syn elimination.

The formed cis olefin has a structure that corresponds to formula II, below, wherein $R^1$, $R^2$ and $R^3$ are as previously defined.

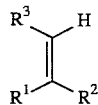

II

A hapten structurally analogous to a substrate is utilized to induce the production of catalytic antibodies. That hapten is referred to herein as an analogue ligand, analogue of the substrate or analogue, and in inducing production of a catalyst molecule, the catalytic paratope also immunoreacts with (binds to) the analogue ligand.

As noted elsewhere, an analogue ligand approximates an unisolatable transition state in the syn elimination reaction. A concerted mechanism has been proposed for an E2 syn elimination contemplated here, so a fully charged species should be absent from the transition state.

A contemplated haptenic molecule contains three structural elements in a particular relation to each other. Those elements are an $R^1$ group and $R^3$ group bonded to adjacent carbon atoms that are bonded to each other by a single bond and are thus analogous to the β- and α-carbon substituents, respectively. The $R^1$ and $R^3$ groups are also bonded in an eclipsed configuration in the analogue ligand. The third structural element is an amino group bonded to the carbon analogous to the β-carbon so that the amine is in a position analgous to $H_β$. That amine group is used to induce the generation of an amino acid residue side chain in the partope that acts as a general base to abstract the proton in the elimination. [See, Janda et al., *J. Am. Chem. Soc.*, 112:1274–1275 (1990).] Less importantly, a hydrogen or substituent group resembling the size of X is bonded to the analogous α-carbon and is in an eclipsed conformation relative to the amine group.

A bicyclic [2.2.2]octane or [2.2.1]heptane ring system is an ideal structure for providing the three important structural features of the analogue ligand. An exemplary analogue ligand has a structure shown in formula III, below.

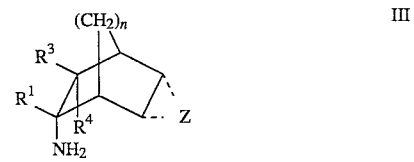

III

In formula III, $R^1$ and $R^3$ are as defined previously, and are the same as $R^1$ and $R^3$ present in the substrate ligand;

$R^4$ is hydrogen or a substituent of about the same size as X;

n is 1 or 2, such that when n is 1, the analogue ligand is a bicyclo[2.2.1]haptane and when n is 2, the analogue ligand is a bicyclo[2.2.2]octane; and Z is a carboxyl-terminated haptenic linking group for bonding the analogue ligand to an immunogenic carrier. Z is bonded to one or the other of the carbon atoms of the compound of formula III to which Z is linked by dotted lines.

The analogue ligand is thus seen to utilize the $R^1$ and $R^3$ substituents that are utilized in the substrate ligand. Thus, where $R^1$ in the substrate is benzoyl, $R^1$ in the analogue is benzoyl, and where $R^3$ is phenyl in one, it is phenyl in the other.

It is noted that a given analogue ligand can induce production of catalystic paratope-containing molecules that can bind to and react with not only a substrate having the exact same $R^1$ and $R^3$ substituent groups but also to a substrate having substituent groups that are similar in size and shape to the $R^1$ and $R^3$ groups of the analogue. Thus, for example, where $R^1$ of the analogue is benzoyl, a substrate can have an $R^1$ group that is benzoyl, 2-, 3- or 4-pyridinecarbonyl, cyclohexylcarbonyl, cyclopentylcarbonyl and the like. The same holds for $R^3$.

Such binding between a substrate other than a molecule having $R^1$ and $R^3$ groups identical to those in the analogue ligand can be readily determined from the Michaelis constant, $K_m$. Exemplary $K_m$ values are about 1–1000 mM.

The $R^4$ substituent is preferably hydrogen. $R^4$ can, however, be another substituent, and when that is the case, $R^4$ preferably has about the size (steric bulk or volume) of the X group. For example, where X is a trimethylammonium group, an $R^4$ that is t-butyl is about the same size.

The Z group is used to link the haptenic analogue ligand to an antigen carrier molecule. Thus, as a hapten, the analogue ligand is not itself immunogenic and must be linked to an immunogenic carrier molecule, usually a protein, to induce the production of antibodies. Depending mostly upon ease of synthesis, the hapten typically is prepared to contain an amine, aminomethyl, carboxyl or preferably, a hydroxyl group that can be coupled to the linker, and that together with the linker is denoted Z. Although the linker is not a structural feature of the haptenic aminomethyl-containing Z group includes a —$CH_2NH$— in place of the —NH— group. The analogue ligand here preferably contains a hydroxyl group and Z is a half-ester of a dicarboxylic acid such as succinic acid.

Exemplary substrates, analogue ligands and cis olefin products are shown in Table 1, below.

TABLE 1

| Substrate[1] | Analogue[1,2] | Product[1] |
|---|---|---|

[1] Ph = phenyl; Naph = naphthyl; cyclo-$C_5$ = cyclopentyl; Cyclo-$C_6$ = cyclohexyl; i-Pr = iso-propyl; $C_7H_{15}$ = n-heptyl.
[2] O-Link = a linker group ester-bonded to the analogue ligand by a reacted hydroxyl group of the analogue ligand.

analogue ligand that is mimicked in the substrate, such mimicking can take place.

It is preferred that the linker be bonded to the carrier molecule via a carboxyl group of the linker. As a consequence, where the hapten contains a carboxyl group for bonding to the linker, —Z, after reaction preferably has the formula —C(O)NH($CH_2$)$_n$$CO_2$H, where n is an integer from 1 to about 9 to provide linkers such as glycine, β-alanine, 6-aminocaproic acid and 10-aminodecanoic acid. Where the hapten contains an amine, aminomethyl or hydroxyl group for bonding to the linker is preferably a $C_4$–$C_6$ straight chain dicarboxylic acid such as glutaric acid, succinic acid, maleic acid, fumaric acid or adipic acid so that —Z as an amide corresponds to the formula —NHC(O)($CH_2$)$_m$$CO_2$H, where m is an integer that is 2–4, or —NHC(O)($CH_2$)$_p$CH=CH($CH_2$)$_q$$CO_2$H where p and q are independently zero or one. Ester —Z groups have similar structures with an —O— replacing —NH—, whereas an Contemplated catalytic monoclonal antibody molecules or their paratope-containing portions bind to a before-defined substrate and analogue ligand, and catalyze the syn elimination of HX from the substrate to form a corresponding cis olefin. The present catalyzed elimination reactions are stereoselective; i.e., a cis olefin is formed. A contemplated catalyzed reaction is also enantioselective; one substrate enantiomer reacts to the exclusion of the other enantiomer.

A contemplated monoclonal paratope-containing molecule (receptor) can be referred to as being biologically active. Biological activity of a receptor molecule is evidenced by the binding of the receptor to its antigenic reactant (substrate) ligand, inhibitor ligand or analogue ligand upon their admixture in an aqueous medium, at least at physiological pH values and ionic strengths. Preferably, the receptors also bind to an antigenic ligand within a pH value range of about 7 to about 10, and at ionic strengths such as that of distilled water to that of about one molar sodium chloride.

The substrate ligand and receptor catalyst molecules are admixed in an aqueous medium. That medium is typically buffered between pH values of about 7 to about 10 and contains salts such as phosphate and 2-(cyclohexylamino) ethane sulfonic acid (CHES) at appropriate concentrations to provide the desired pH value and preserve protein structure, as is well known.

A contemplated aqueous medium can also contain up to about 20, and more preferably about 10 to about 15, volume percent of a water-miscible organic solvent that does not itself react with or denature the protein catalyst. Exemplary solvents include methanol, ethanol, acetonitrile, isopropanol, DMF and DMSO.

Use of a two-phase aqueous/water-immiscible organic solvent reaction medium as was utilized in Janda et al., Science, 259:490–493 (1993), citation 22, is also contemplated. See, also Ashley et al., J. Org. Chem., 57:6691–6693 (1992), and the citations therein. That biphasic medium included 5 volume percent of a buffered aqueous solution and 95 volume percent hexane.

The aqueous medium typically has a pH value of about 7 to about 10, and preferably about pH 8.0 to about 9.0. pH Values greater and less than those recited values can also be utilized so long as the catalyzed reaction is not substantially interfered with or inhibited.

The catalytic reactions are typically carried out at ambient room temperature; i.e., at about 20° to about 25° C., or at 37° C., and at an ambient atmospheric pressure; i.e., at about one atmosphere. However, temperatures down to about the freezing point of the aqueous medium and up to about the boiling point of the medium at atmospheric pressure can also be used. As is known, proteins such as the receptor molecule tend to denature at elevated temperatures such as those at which an aqueous medium boils, e.g., at about 100° C. and thus temperatures below about 50° C. are preferred. As is also well known, reactions that follow multimolecular kinetic expressions such as the syn elimination contemplated here decrease in rate as the temperature decreases. Thus, a minimal temperature of about 15° C. is preferred.

The biological reaction conditions are the temperature, pH value and presence of salts discussed above and in regard to a receptor molecule being biologically active.

The reactant ligand (substrate) is present in a reaction mixture in an amount up to its solubility in the aqueous medium. Normally used concentrations of the reactant ligand (substrate) are about 0.1 micromolar (μM) to about 10 millimolar (mM), with that amount also being a function of the solubility of the reactant ligand in the solvent medium. Where the product is desired, per se, relatively higher concentrations are used as compared to lower concentrations where a reaction mechanism or reaction kinetics are to be studies.

An effective amount of the catalytic receptor molecule is also present. That effective amount is typically a catalytic amount; i.e., the receptor is used at a molar ratio to the reactant ligand of about 1:2 to about 1:10,000, with a molar ratio of about 1:10 to about 1:100 being preferred. The ratio of receptor molecule to reactant ligand typically depends upon the specific activity of the receptor molecule toward the reactant ligand and the purpose of the user in running the reaction.

Thus, where the product is desired, a relatively higher concentration of receptor and higher receptor to reactant ligand ratio are used. Where the reaction mechanism or kinetics of the reaction are being studied, a lower concentration and ratio are typically used. A stoichiometric amount of receptor or more can also be used, but since the receptor is a catalytic molecule, use of even a stoichiometric amount can be wasteful. Thus, at least a catalytic amount of the receptor is utilized.

The admixture formed by admixing reactant ligand molecules and receptor molecules in an aqueous medium is maintained for a time period sufficient for the binding and reaction to occur; i.e., for the cis olefin to be formed. The duration of that maintenance period is a function of several parameters including the receptor and reactant ligand selected, their concentrations, pH value, and temperature, as well as what is being sought from the reaction.

Thus, where kinetic studies are being carried out, maintenance times of minutes to hours are frequently used. Where the reaction products are desired, maintenance times of hours to days are more usual.

The cis olefin produced in a contemplated reaction is preferably recovered. Such recovery is not, however, required, as the olefin can be used in situ.

A formed cis olefin product can be easily recovered. The desired product can be recovered using chromatographic techniques described herein. It can also be useful to extract the product with a water-immiscible organic solvent such as dichloromethane, benzene or ethyl acetate prior to chromatographic separation.

A contemplated preferred hapten is prepared by use of cyclopentadiene or cyclohexadiene in a Diels-Alder reaction with a suitably cis-di or tri-substituted nitroethylene (nitroolefin) derivative. Such a reaction is shown illustratively in Scheme 1 below, wherein n is 1 or 2 and $R^1$, $R^3$ and $R^4$ are as described before.

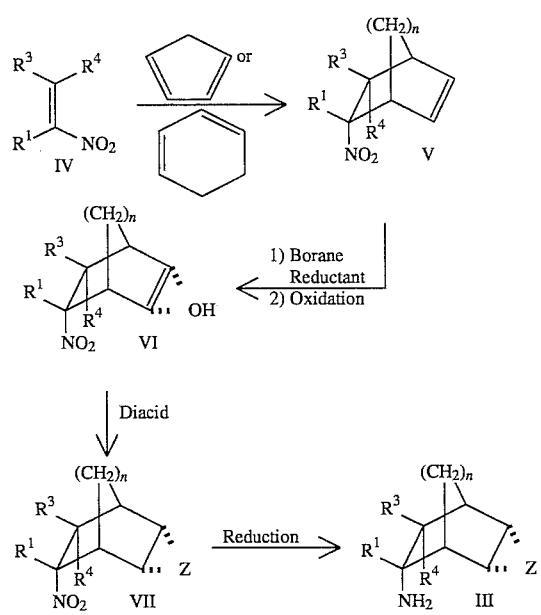

Scheme 1

Thus, following the reactions of Scheme 1, a nitro-olefin compound of formula IV is reacted under Diels-Alder conditions with cyclopentadiene or cyclohexadiene to form the [4+2] bicylo[2.2.1]heptane (n=1) or bicyclo[2.2.2]octane (n=2) adduct that is a compound of formula V. Reduction of a compound of formula V ethylenic double bond with a borane reductant such as 9-borabicyclo[3.3.1]nonane (9-BBN) in THF, diborane or sodium borohydride followed by oxidation of the adduct with a suitable oxidant such as hydrogen peroxide provides the isomeric alcohols (a compound of formula VI) that are both shown by dotted bond lines to the hydroxyl group.

The two isomers of formula VI are preferably isolated and separated prior to carrying out the next reaction, although separation can occur after esterification. Separation of the two isomers is not necessary for use of the ultimately produced hapten, but separation is preferred.

Esterification of a compound of formula VI with a carboxylic diacid or diacid precursor such as succinic anhydride, glutaric anhydride or adipic anhydride, succinimidyl adipoyl or glutaroyl or succinoyl chloride forms a compound of formula VII. Reduction of the nitro group of a compound of formula VII, preferably with Raney nickel (Raney Ni), provides the hapten of formula III. The hapten is recovered for use.

The cis di- or tri-substituted nitroolefin is readily prepared by reaction of an $R^1$-substituted nitromethane compound and an $R^3,R^4$-substituted aldehyde (where $R^4$ is hydrogen) or ketone in the presence of methylamine in ethanol. The intermediate N-methyl $R^1,R^4$-containing imine can also be preformed and then reacted with the $R^1$-substituted nitromethane.

III. Results

For acyclic systems, it is generally accepted that antiperiplanar elimination is greatly favored over syn elimination. [March, *Advanced Organic Chemistry*, John Wiley & Sons, New York, pp. 874–880 (1985).] Although the eclipsed syn coplanar transition state may be preferentially adopted over the staggered antiperiplanar transition state in constrained cyclic systems, Kwart et al., *J. Am. Chem. Soc.*, 86:2606–2611 (1964); Cooke et al., *J. Am. Chem. Soc.*, 90:5556–5561 (1968), acyclic syn elimination is rare. Additionally, all accounts of acyclic syn elimination have been shown to provide a trans (E) olefin, resulting when the competing anti elimination suffers significant destabilizing steric interactions enroute to the alternative cis olefin. [Bailey et al., *J. Am. Chem. Soc.*, 92:6904–6910 (1970); Bailey et al., *J. Am. Chem. Soc.*, 92;6911–6913 (1970).] In fact, of the four possible elimination pathways (anti to trans, anti to cis, syn to trans, and syn to cis), syn elimination to a cis olefin is regarded as the least favored transformation of the group, and has not yet been selectively achieved in an acyclic system. [Bartsch et al., *J. Chem. Rev.*, 80453–494 (1980); Borchardt, et al., *J. Amer. Soc.*, 96:3918–3910 (3920).]

Consistent with these generalizations, substrate Compound 1 undergoes anti elimination to give exclusively the trans olefin Compound 3 (Scheme 2). Reaction conditions: 15 percent aq DMSO, 100 mM CHES buffer, pH 9.0, 37° C. No isomerization of either olefinic product (Compounds 3 or 4) was observed under these conditions.

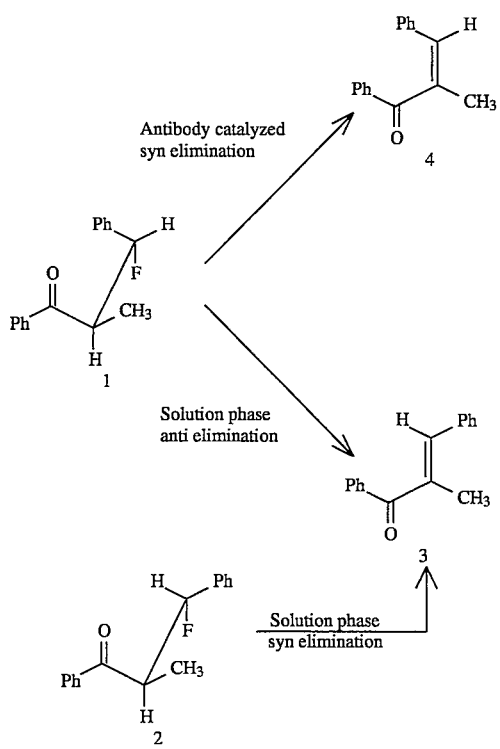

Scheme 2

The design of hapten Compound 5 was intended to elicit antibodies that would bind and lock substrate Compound 1 in an eclipsed conformation, such that subsequent elimination would occur syn to afford selectively the cis olefin product Compound 4. The bicyclo[2.2.1]heptane ring structure of hapten Compound 5 ensured presentation of the phenyl and benzoyl substituents in the desired eclipsed arrangement, as opposed to a cyclohexyl framework that would have oriented these substituents in a gauche relationship.

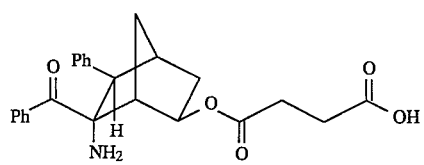

5

The primary amine of Compound 5 was introduced in a position corresponding to the α-keto proton of substrate Compound 1 to induce an amino acid side chain in the antibody binding pocket capable of acting as a general base for the abstraction of this proton, as noted before. [Shokat et al., *Nature*, 338:269–271 (1989); Janda et al., *J. Am. Chem. Soc.*, 112:1274–1275 (1990); Janda, *Biotechnol. Prog.*, 6:178 (1990); Janda et al., *J. Am. Chem. Soc.*, 113:5427–5434 (1991)].

Compounds 1–5 were synthesized as discussed herein, and the hapten Compound 5 was conjugated to carrier protein keyhole limpet hemocyanin (KLH). In a control study, Compound 5 was shown to react exclusively with benzylamine under the following conditions: (1) EDCI (1.05 eq), N-hydroxysuccinimide (1.5 eq), DMF, 25° C., 7 hours; (2) benzylamine (1.5 eq), room temperature, 10 hours. No amine acylation of Compound 5 was observed under these conditions.

Immunization with the KLH conjugate and generation of monoclonal antibodies were performed as described hereinafter. Twenty-six monoclonal antibodies specific for Compound 5 were assayed for catalysis. The rate of elimination of substrate Compound 1 to product Compounds 3 or 4 was assayed in the absence and presence of antibody at 37° C. Thus, a solution of antibody in 100 mM CHES buffer, pH 9.0 at 37° C., was treated with substrate Compound 1 in DMSO to provide a final solution containing 5 mM antibody in 15 percent aqueous DMSO, 100 mM CHES, pH 9.0. All reaction rates were determined by analytical reverse phase HPLC (Vydac-$C_{18}$, 41 percent acetonitrile in $H_2O$/0.1 percent trifluoroacetic acid) by measuring product formation relative to 4-methyl-3-nitroanisole as a standard.

In the absence of antibody, only product Compound 3 was generated with a first order rate constant of $2.48 \times 10^{-4}$ $min^{-1}$. One of the 26 antibodies, 1D4, was found to catalyze exclusively the syn elimination of substrate Compound 1 to cis product Compound 4. No detectable difference was observed between the rate of formation of the trans product Compound 3 in the 1D4-catalyzed versus uncatalyzed reactions. In a control experiment, 1D4 showed no capacity to isomerize either olefinic product under the reaction conditions described.

Hybridoma 1D4 that secretes antibody 1D4 was deposited with the American Type Culture Collection (ATCC), 12301 Parklawn Drive, Bethesda, Md. on Aug. 17, 1994, and was given accession number HB 11704.

The present deposit was made in compliance with the Budapest Treaty requirements that the duration of the deposit should be for 30 years from the date of deposit or for five years after the last request for the deposit at the depository or for the enforceable life of as U.S. patent that matures from this application, whichever is longer. The hybridoma will be made available to the public without restriction upon the issuance of a patent from this application. The hybridoma will be replenished should it become non-viable at the depository.

The initial rate of syn elimination by 1D4, when measured as a function of substrate Compound 1 concentrations followed Michaelis-Menten kinetics. The kinetic constants $K_m$ and $k_{cat}$ were determined to be 212 μM and $2.95 \times 10^{-3}$ $min^{-1}$, respectively. The catalytic activity of 1D4 was competitively inhibited by the addition of hapten Compound 5, indicating that catalysis occurs within the antibody binding pocket.

The rate acceleration ($k_{cat}/k_{uncat}$) due to 1D4 catalysis could not be determined because in the absence of antibody, formation of the cis product Compound 4 was immeasurably slow under our reaction conditions. Catalysis of the syn elimination of substrate Compound 1 in the absence of an observable $k_{uncat}$ underscores the power of catalytic antibodies to accelerate energetically demanding reactions with high efficiency and selectivity.

Antibody 1D4 was also assayed for its capacity to catalyze the anti-elimination of substrate Compound 2 to afford the product cis olefin Compound 4. Interestingly, under the background conditions described previously, substrate Compound 2, like substrate Compound 1, eliminates entirely to the trans olefin Compound 3. No isomerization was witnessed for either product Compounds 3 or 4 under these conditions, and therefore, the conversion of Compounds 2 to 3 may be regarded as a syn elimination.

In the absence of antibody, elimination of either substrate Compounds 1 or 2 to provide exclusively the trans olefin Compound 3 is consistent with previous work, and may reflect primarily the distinct thermodynamic advantage Compound 3 holds over its cis counterpart Compound 4. The anti-elimination of Compound 2, which would proceed through a staggered transition state to provide product Compound 4, should be quite favored over the syn elimination of substrate Compound 1, which requires reaction through an eclipsed transition state to provide Compound 4. Bartsch et al., Chem. Rev., 80:453–494 (1980); Quast et al., Chem Ber., 115:1525–1546 (1982). Yet, monoclonal antibody 1D4 demonstrates the reversed selectivity in that it accelerates the syn elimination of Compound 1 to product Compound 4 more efficiently than the anti-elimination of Compound 2 to product Compound 4.

This intriguing result emphasizes the fidelity of monoclonal 1D4 for the eclipsed conformation of substrate Compound 1, in accord with the bicyclo[2.2.1]heptane ring structure of the inducing hapten Compound 5. In essence, the binding energy of 1D4 has been directed towards recognition of the phenyl and benzoyl substituents of substrates Compounds 1 and 2 in an eclipsed orientation. Consequently, 1D4 appears more willing to permit the syn elimination of Compound 1 from this conformation, than the rearrangement of Compound 2 to the staggered transition state required for the otherwise preferred anti elimination. Mechanistic investigations of 1D4 are underway to determine more precisely how the antibody performs the syn elimination reaction.

Preliminary estimates of the energy difference between the anti and syn elimination reactions of Compound 1 to product Compounds 3 and 4, respectively, indicate an up to 5 kcal separation, likely making syn elimination of Compound 1 to product Compound 4 the most energetically demanding reaction yet catalyzed by an antibody. Thus, the generation of an antibody capable of accelerating a highly disadvantaged syn elimination reaction has brought the level of "disfavored" chemistry amenable to antibody catalysis to a new extreme.

IV. preparation of Conjugates and Inocula

Conjugates of haptenic analogue ligand molecules with antigenic (immunogenic) protein carriers such as keyhole limpet hemocyanin (KLH) can be prepared, for example, by activation of the carrier with a coupling agent such as MBS (m-maleimidobenzoyl-N-hydroxy succinimide ester), and coupling to the thiol group of the analogue ligand. See, for example, Liu et at., Biochem., 80, 690 (1979). As is also well known in the art, it is often beneficial to bind a compound to its carrier by means of an intermediate, linking group.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

The choice of carrier is more dependent upon the ultimate intended use of the antigen than upon the determinant portion of the antigen, and is based upon criteria not particularly involved in the present invention. For example, if the conjugate is to be used in laboratory animals, a carrier that does not generate an untoward reaction in the particular animal should be selected.

The carrier-hapten (carrier-analogue ligand) conjugate is dissolved or dispersed in an aqueous composition of a physiologically tolerable diluent such as normal saline, PBS, or sterile water to form an inoculum. An adjuvant such as complete or incomplete Freund's adjuvant or alum can also be included in the inoculum. The inoculum is introduced as by injection into the animal used to raise the antibodies in an amount sufficient to induce antibodies, as is well known.

Thus, a hapten-linker conjugate such as a compound of formula III like Compound 5 is coupled to the immunogenic carrier using usual procedures. The inker is a carboxy-terminated linker that preferably contains 4 to 6 carbon atoms. The linker is preferably prepared from a dicarboxylic acid or a diacid precursor such as an anhydride, diacid chloride, or an acid chloride/half-ester such as a compound discussed previously herein.

V. Preparation of Monoclonal Receptors

The foregoing KLH conjugates (about 100 µg) were used to immunize mice (129G1X* strain), and monoclonal antibodies were obtained as described by Niman et al., *Proc. Natl. Acad. Sci. USA*, 77, 4524 (1980) and Niman et al., in *Monoclonal Antibodies and T-Cell Products*, Katz, D. H. ed., 23–51, CRC Press, Boca Raton, Fla. (1982). The lymphocytes employed to form the hybridomas of the present invention can be derived from any mammal, such as a primate, rodent (e.g., mouse or rat), rabbit, guinea pig, cow, dog, sheep, pig or the like. As appropriate, the host can be sensitized by injection of the immunogen, in this instance a haptenic analogue ligand, followed by a booster injection, and then isolation of the spleen.

It is preferred that the myeloma cell line be from the same species as the lymphocytes. Therefore, fused hybrids such as mouse-mouse hybrids [Shulman et al., *Nature*, 276, 269 (1978)] or rat-rat hybrids [Galfre et al., *Nature*, 277, 131 (1979)] are typically utilized. However, some rat-mouse hybrids have also been successfully used in forming hybridomas [Goding, "Production of Monoclonal Antibodies by Cell Fusion," in *Antibody as a Tool*, Marchalonis et al., eds., John Wiley & Sons Ltd., p. 273 (1982)]. Suitable myeloma lines for use in the present invention include MPC-11 (ATCC CRL 167), P3X63-Ag8.653 (ATCC CRL 1580), Sp2/0-Ag14 (ATCC CRL 1581), P3X63Ag8U.1 (ATCC CRL 1597), Y3-Agl.2.3. (deposited at Collection Nationale de Cultures de Microorganisms, Paris, France, number 1-078) and P3X63Ag8 (ATCC TIB 9). The non-secreting murine myeloma line Sp2/0 or Sp2/0-Ag14 is preferred for use in the present invention.

The hybridoma cells that are ultimately produced can be cultured following usual in vitro tissue culture techniques for such cells as are well known. More preferably, the hybridoma cells are cultured in animals using similarly well known techniques with the monoclonal receptors being obtained from the ascites fluid so generated. The animals used for generation of the ascites fluid were female 129G1X* mice bred in the mouse colony of The Scripps Research Institute, La Jolla, Calif.; however, when animals other than mice are used for preparation of the hybridomas, mice or that animal type can be used for the production of ascites fluid.

In particular, an exemplary monoclonal receptor is produced by the standard hybridoma technology of Kohler et al., *Nature*, 256, 495 (1975) and Enguall, E., *Methods Enzymol.*, 70, 419 (1980). Specifically, female 129GIX* mice are immunized by intraperitoneal injection with an inoculum of 100 micrograms of conjugate (e.g., Compound 5 linked to KLH) mixed with RIBI adjuvant (MPL and TDM emulsion). Two weeks later, the mice are again injected in a like manner with 50 micrograms of the foregoing conjugate in PBS/alum. After an additional four-eight weeks, the mice are immunized intravenously with 50 micrograms of the conjugate. The spleens are removed from the mice, and the spleen cells were fused to myeloma cells.

The spleens cells are pooled and a single cell suspension is made. Nucleated spleen cells (about $1.4 \times 10^8$) were then fused with about $1.4 \times 10^2$ Sp2/0 and about $2.3 \times 10^8$ HL non-secreting myeloma cells in the presence of a cell fusion promoter (polyethylene glycol 2000). A hybridoma that produces a particular monoclonal antibody was selected by seeding the spleen cells in 96-well plates. Each well contains 150 µl Dulbecco's modified Eagle medium (DMEM) plus 2 percent bovine serum albumin (BSA, 1 percent nutridoma) hypoxanthine, aminopterin and thymidine (i.e., HAT medium) which does not support growth of the unfused myeloma cells.

After two to three weeks, the supernatant above the cell clone in each well is sampled and tested by an ELISA assay (enzyme linked immunosorbent assay as described hereafter) for the presence of antibodies against Compound 5 bound to BSA. Positive wells are cloned twice by limiting dilution. Those clones that continue to produce Compound 5-specific antibody after two clonings are expanded to produce larger volumes of supernatant fluid. The hybridoma and the monoclonal receptors produced therefrom and described herein are identified by the laboratory designation as discussed herein.

The procedures used here for preparation of the conjugate, immunization and hybridoma formation and screening were those reported in Janda et al., *Science*, 244:437–440 (1989).

A monoclonal receptor of the present invention can also be produced by introducing, as by injection, the hybridoma into the peritoneal cavity of a mammal such as a mouse. Preferably, as already noted, syngeneic or semi-syngeneic mammals are used, as in U.S. Pat. No. 4,361,549, the disclosure of which is incorporated herein by reference. The introduction of the hybridoma causes formation of antibody-producing hybridomas after a suitable period of growth, e.g. 1–2 weeks, and results in a high concentration of the receptor being produced that can be recovered from the bloodstream and peritoneal exudate (ascites) of the host mouse.

Although the host mice also have normal receptors in their blood and ascites, the concentration of normal receptors is typically only about five percent that of the monoclonal receptor concentration.

Monoclonal receptors are precipitated from the ascitic fluids, purified by anion exchange chromatography, and dialyzed against three different buffers. The procedures used are as described in Janda et al., *Science*, 259:490–493 (1993).

Antibodies obtained are judged to be greater than 95 percent homogeneous by sodium dodecyl sulfate polyacrylamide gel electrophoresis [Laemmli, V. *Nature*, 227: 680 (1970)]. The resulting concentrated solutions containing isolated IgG fractions were typically prepared into stock solutions of receptor at 1–20 mg/ml using an appropriate buffer such as 50 mM Tris-HCl BisTris or sodium phosphate containing 0.01M sodium azide.

A Fab fragment of a monoclonal receptor can be prepared from the purified receptor using predigested papain in a 0.1M sodium acetate buffer, at a pH value of 5.5, at 37° C., followed by reaction with iodoacetamide. The Fab fragment is typically further purified by anion exchange chromatography, dialysis, and DEAE anion exchange chromatography, and its homogeneity is judged by gel electrophoresis.

VI. Enzyme-linked Immunosorbent Assay (ELISA)

The binding of an analogue ligand by the induced monoclonal receptor molecule is assayed by ELISA with antibody at a fixed concentration in the range of its titer and varying inhibitor (Compound 5) concentration. Use of Compound 5 as inhibitor helps to assure that an observed binding interaction is antigen-specific.

Assays are performed in flat-bottom polyvinyl microtiter plates (Dynatech, Alexandria, Va.). Illustratively, the wells are coated with a solution comprising Compound 5 bonded to BSA as the antigen ligand in phosphate buffered saline (PBS) using 50 microliters of solution per well. BSA is used as a carrier to bind the hapten to the cell wall, and an analogue ligand/BSA conjugate is used in place of the immunizing KLH-containing conjugate to screen out possible anti-KLH antibodies.

The bound ligands are coated at 1 microgram per milliliter. The plates are then incubated overnight at 37° C. in a dry oven. The dried plates are stored at 4° C. until use. Prior to the ELISA assay, dried plates are rehydrated by two washes of two minutes each with ten millimolar (mM) PBS, pH 7.4, containing 0.1 percent polyethylene sorbitan monolaureate (Tween 20) and 0.02 percent Thimerosal (sodium ethylmercurithiosalicylate), (Sigma, St. Louis, Mo.).

In order to reduce non-specific binding, hybridoma supernatants are diluted 1:2 in washing buffer containing 0.1 percent BSA as diluent. Fifty microliters of diluted hybridoma supernatants are thereafter added to each well and incubated for one hour at 4° C. on a gyroshaker to contact the monoclonal antibody-containing supernatant with the bound Compound 5. Following two washes of two minutes each, 50 microliters of peroxidase-labeled goat anti-mouse IgG+IgM (Tago, Burlingame, Calif.), diluted 1:1000, are added to each well, and the reaction mixture is incubated at 4° C. for one hour to bind the labeled antibody to bound monoclonal antibody.

The substrate used to assay bound peroxidase activity is prepared just prior to use and consists of 400 microgram/ml o-phenylenediamine (Sigma, St. Louis, Mo.) in 80 mM citrate-phosphate buffer, pH 6.0, containing 0.12 percent $H_2O_2$. After two final washes, 50 microliters of substrate solution are added to each well, and color is allowed to develop for 15 minutes in the dark. Color development is stopped by adding 25 microliters of four molar $H_2SO_4$ to each well and the optical density at 492 nanometers (nm) is measured with a Multiskan ELISA plate reader.

For another preparation of the receptor molecules, the gene that encodes an antibody combining site-forming fragment can be obtained from any cell that produces an antibody molecule that immunoreacts as discussed herein. A preferred cell is a hybridoma cell.

For examples of general recombinant DNA cloning methods, see *Molecular Cloning*, Maniatis et al., Cold Spring Harbor Lab., New York, 1982; *DNA Cloning*, Glover, ed., IRL Press, McLean Va. (1985). For the genomic cloning and expression of immunoglobulin genes in lymphoid cells, see Neuberger et al., *Nature*, 312:604–8 (1984); Ochi et al., *Proc. Natl. Acad. Sci. USA*, 80:6351–55 (1987); and Oi et al., *Proc. Natl. Acad. Sci. USA*, 80:825–29 (1983). For cloning of immunoglobulin genes from hybridoma cells and expression in *Xenopus oocytes*, see Roberts et al., *Protein Engineering*, 1:59–65 (1986), and see Wood et al., Nature, 314:446–9 (1985) for expression in yeast.

VII. Syntheses

For Compounds 1 and 2, 3-hydroxy-2-methyl-1,3-diphenyl-1-propanone was prepared as discussed in Brown et al., *J. Org. Chem.*, 57:499–504 (1992), and then treated with diethylaminosulfur to trifuoride (DAST); 1.1 equiv.) in $CH_2Cl_2$ at −78° C. for one hour to provide a 4:1 mixture of Compounds 2 and 1, respectively. Flash chromatography (1–4 percent ether in hexanes) clearly separated Compounds 1 and 2, which were identified by NMR correlation with the corresponding bromides.

Reaction of either of Compounds 1 or 2 with one equivalent of KOH in methanol provided exclusively the trans product, Compound 3. Compound 3 was isomerized under U.V. light (five hours in benane) to yield a 3:1 mixture of Compounds 4 and 3, respectively. The authentic samples of Compounds 3 and 4 were clearly separated by flash silica gel chromatography using 1–2 percent ether in hexanes as solvent.

Details of the synthesis of Compound 5, the hapten utilized to elicit monoclonal antibodies that catalyze the syn. elimination of Compound 1 to provide the cis olefin Compound 4 are provided hereinafter. Key to the design of hapten Compound 5 was the rigid eclipsed conformation embodied in the bicyclo[2.2.1]heptane ring system that dictated the presentation of the benzoyl and phenyl substituents in the desired eclipsed arrangement and the primary amine of Compound 5 that was used to induce an antibody functionality capable of acting as a base in the abstraction of the α-proton of Compound 1. These synthetic rections are outlined in Scheme 3, below, and in the specific syntheses that follows.

Scheme 3

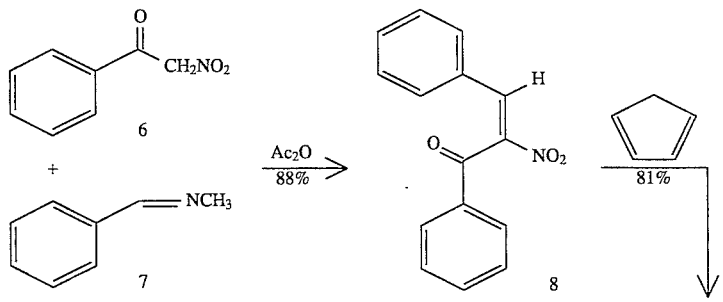

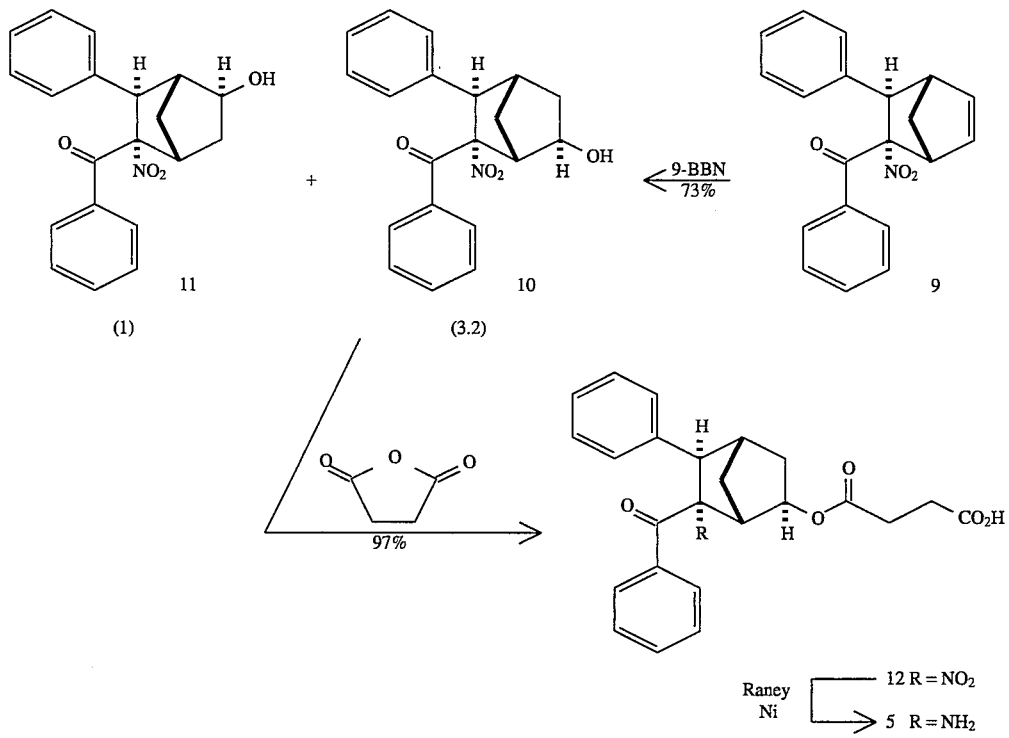

-continued
Scheme 3

Condensation of α-nitroacetophenone (Compound 6) with N-methyl benzylidene imine (Compound 7) under the conditions detailed by Dornow et al., Ann., 588:40 (1954) (1.1 equiv. Ac$_2$O, Et$_2$O, reflux, 3 hours, 88 percent) provided (E)α-nitrochalcone (Compound 8) as the exclusive olefin isomer detected in the reaction mixture (Scheme 3). Treatment of Compound 8 with freshly cracked cyclopentadiene (9.0 equiv. 45° C., CH$_2$Cl$_2$ 24 hours, 81 percent) provided a single predominant Diels-Alder adduct, Compound 9, derived from a [4+2] cycloaddition reaction through a transition state with the nitro substituent endo to the diene. Less than 1–3 percent of the diastereomeric exo adduct was detected. Notably, this Diels-Alder reaction proceeds almost exclusively to provide the sterically less favored adduct, Compound 9, presumably a consequence of a strong endo directing effect of the polarized nitro substituent. Use of cyclohexadiene in the place of cyclopentadiene provides the corresponding bicyclo[2.2.2]octane derivative.

Clean exo hydroboration of Compound 9 (1.25 equiv. 9-BBN, THF, 25° C., 10 hours; NaOH-H$_2$O$_2$, 73 percent) followed by oxidative workup provided a readily separable 3.2:1 mixture of Compounds 10 and 11. Acylation of Compound 10 with succinic anhydride (2.0 equiv., 0.1 equiv. DMAP, CH$_2$Cl$_2$, 25° C., 4 hours, 97 percent) cleanly provided the hemisuccinate Compound 12 as a highly crystalline intermediate. Single-crystal X-ray structure analysis of Compound 12 unambiguously established its structure confirming both the endo diastereoselectivity of the Diels-Alder reaction providing Compound 9 and the regioselectivity of the exo hydroboration reaction to provide Compound 10.

Finally, reduction of the nitro group of Compound 12 to an amine (Raney Ni, H$_2$, CH$_3$OH—H$_2$O, 45° C., 20 hours) provided Compound 5 along with variable amounts of the product resulting from complete reduction to the corresponding hydrocarbon with loss of the nitro group. Alternative reduction methods including the use of H$_2$—Pd/C (3 atm H$_2$, CH$_3$OH and CH$_3$OH—THF 9:1; 25° C., 1–20 hours), H$_2$—PtO$_2$ (3 atm H$_2$, CH$_3$OH-THF 9:1, 25° C., 5 hours), or transfer hydrogenation (HCO$_2$NH$_4$—Pd/C) afforded mixtures including the hydroxylamine and hydrocarbon. NiCl$_2$—NaBH$_4$, FeCl$_2$—HOAc, TiCl$_4$—LiAlH$_4$, Na$_2$S$_2$O$_4$ and Ni(OAc)$_2$—BER provided mainly recovered Compound 12, and Al/Hg reduction (THF—H$_2$O or CH$_3$OH—H$_2$O 8:1, 25° C.) afforded a mixture including the hydroxylamine and the amino alcohol resulting from the additional ketone reduction of Compound 5.

EXAMPLE 1

(1S*,2R*,3S*,4R*)-2-Benzoyl-2-nitro-3-phenylbicyclo[2.2.1]hept-5-ene (Compound 9)

A solution of (E)α-nitrochalcone [Dornow et al., Ann., 588:40 (1954); Yamamura et al., Bull. Chem. Soc., Jpn. 44:2440 (1971)] (Compound 7, 5.35 g, 21.1 mmol) in a minimum amount of CH$_2$Cl$_2$ (2–3 mL) was treated with freshly cracked cyclopentadiene (15.7 mL, 190 mmol, 9.0 equiv. ). The reaction mixture was stirred at 45° C. for 24 hours before the mixture was partitioned between CH$_2$Cl$_2$ (200 mL) and H$_2$O (200 mL). The CH$_2$Cl$_2$ layer was dried (Na$_2$SO$_4$) and concentrated under reduced pressure. Chromatography (SiO$_2$, 5×15 cm, 5 percent Et$_2$O-hexane eluant) afforded Compound 9 (5.45 g, 6.73 g theoretical, 81 percent) as a white crystalline solid: mp 119°–120° C. (Et$_2$O-hexane, colorless needles); $^1$H NMR (CDCl$_3$, 250 MHz) δ7.33 (d, 2H, J=8.0 Hz), 7.25–6.97 (m, 8H), 6.72 (m, 1H, C6-H), 5.99 (m, 1H, C5-H), 4.24 (d, 1H, J=2.7 Hz, C3-H), 3.84 (s, 1H, C1-H), 2.93 (s, 1H, C4-H), 2.65 (d, 1H, J=9.8 Hz, C7-H syn to ketone), 1.86 (d, 1H, J=9.9 Hz, C7-H anti to ketone); $^{13}$C NMR (CDCl$_3$, 62.5 MHz) δ192.5, 144.3, 137.9, 134.2, 133.7, 133.0, 129.0, 128.6, 128.4, 127.9, 127.5, 105.4, 54.8, 53.5, 51.1, 48.5; IR (neat) $v_{max}$ 3004, 2970, 1685, 1540, 1465, 1354, 1240 cm$^{-1}$; FABHRMS (NBA-NaI) m/e 342.1101 ($C_{20}H_{17}NO_3$+Na+ requires 342.1106). A mixture of minor diastereomers (<3 percent) was isolated in trace amounts. Anal. Calcd for $C_{20}H_{17}NO_3$: C, 75.22; H, 5.37; N, 4.39. Found: C, 74.85; H, 5.29; N, 4.55.

EXAMPLE 2

(1R*,2S*,4R*,5S*,6S*)-6-Benzoyl-2-hydroxy-6-nitro-5-phenylbicyclo[2.2.1]heptane (Compound 10)

A solution of Compound 9 (2.20 g, 6.90 mmol) in THF (18 mL, 0.38M) was treated with 9-BBN (8.62 mmol, 1.25 equiv) in THF (17.25 mL, 0.5M) and the mixture was allowed to stir at 25° C. under $N_2$ for 10 hours. The resulting mixture was treated successively with 4.15 mL of EtOH, 1.5 mL of 20 percent aqueous NaOH, and 1.65 mL of 50 percent aqueous $H_2O_2$. The reaction solution was warmed at 50° C. for one hour, recooled to 25° C., and partitioned between EtOAc (200 mL) and $H_2O$ (200 mL). The EtOAc layer was dried ($Na_2SO_4$) and concentrated under reduced pressure. Chromatography ($SiO_2$, 5×15 cm, 10–25 percent EtOAc-hexane gradient elution) afforded the major isomer Compound 10 (1.29 g, 55.5 percent; $R_f$=0.32, 20 percent EtOAc-hexane) and Compound 11 (1S*,2R*,4S*,5R*,6S*-5-benzoyl-2-hydroxy-5-nitro-6-phenyl-bicyclo[2.2.1]heptane, 400 mg, 17.2 percent; $R_f$=0.26, 20 percent EtOAc-hexane) as white solids cleanly separated from one another in a 3.2:1 ratio (1.69 g total, 2.32 g theoretical, 73 percent). For Compound 10: mp 168°–169° C. (EtOAc-hexane, colorless needles); $^1$H NMR (CDCl$_3$, 250 MHz) δ7.38 (d, 2H, J=8.2 Hz), 7.31–6.94 (m, 8H), 4.33 (d, 1H, J=2.4 Hz, C5-H), 3.85 (d, 1H, J=6.8, C2-H), 3.29 (s, 1H, C1-H), 2.63 (d, J=11.3 Hz, C7-H syn to ketone), 2.46 (d, 1H, J=4.3 Hz, C4-H), 2.26–2.16 (m, 2H), 1.67–1.60 (m, 2H); $^{13}$C NMR (CDCl$_3$, 50 MHz) δ189.9, 138.8, 133.7, 133.0, 128.9, 128.5, 128.3, 127.8, 127.4, 105.0, 69.3, 55.5, 55.4, 44.6, 42.1, 35.7; IR (neat) $v_{max}$ 3331, 2968, 2900, 1689, 1538, 1444, 1353, 1234, 1096, 1063 cm$^{-1}$; FABHRMS (NBA-NaI) m/e 360.1230 (C20H19NO4+Na$^+$ requires 360.1212). Anal. Calcd for $C_{20}H_{19}NO_4$: C, 71.20; H, 5.68; N, 4.15. Found: C, 71.13; H, 5.89; N, 4.10. For Compound 11: $^1$H NMR (CDCl$_3$, 250 MHz) δ7.34 (d, 2H, J=8.0 Hz), 7.25–6.90 (m, 8H), 4.18 (m, 2H), 3.25 (m, 1H), 2.62 (d, 1H, J=11.2 Hz), 2.26 (s, 1H), 2.12 (d, 1H, J=11.4 Hz), 1.80–1.62 (m, 2H), 1.45 (m, 1H); FABHRMS (NBA-CsI) m/e 470.0368 ($C_2H_{19}NO_4$+Cs$^+$ requires 470.0368).

EXAMPLE 3

(1R*, 2S*, 4R*, 5S*, 6S*)-6-Benzoyl-6-nitro-5-phenylbicyclo[2.2.1]heptane-2-hemisuccinate (Compound 12)

A solution of Compound 10 (950 mg, 2.82 mmol, 1.0 equiv) in CH$_2$Cl$_2$ (9.4 mL, 0.3M) was treated sequentially with succinic anhydride (564 mg, 5.64 mmol, 2.0 equiv), Et$_3$N (0.786 mL, 5.64 mmol, 2.0 equiv), and DMAP (95 mg, 0.1 wt equiv), and the reaction mixture was stirred at 25° C. for 4 hours. The reaction mixture was partitioned between CH$_2$Cl$_2$ (200 mL) and H$_2$O (200 mL) and the organic layer was washed with aqueous 1N HCl (150 mL), dried (Na$_2$SO$_4$), and concentrated under reduced pressure. Chromatography (SiO$_2$, 5×15 cm, 0–5 percent CH$_3$OH—CH$_2$Cl$_2$ gradient elution) afforded Compound 12 as a colorless foam (1.20 g, 1.23 g theoretical, 97 percent): mp 172°–173° C. (EtOAc-hexane, colorless needles); $^1$H NMR (CDCl$_3$, 250 MHz) δ7.38 (d, 2H, J=9.5 Hz), 7.31–6.95 (m, 8H), 4.67 (d, 1H, J=6.7 Hz, C2-H), 4.39 (d, 1H, J=2.4 Hz, C5-H), 3.45 (s, 1H, C1-H), 2.74–2.60 (m, 5H), 2.49 (d, 1H, J=3.1 Hz, C4-H), 2.33 (m, 1H, C3-H), 2.12 (d, 1H, J=11.5 Hz, C7-H anti to ketone), 1.73 (dd, 1H, J=9.8, 2.2 Hz, C3-H); $^{13}$C NMR (CDCl$_3$, 50 MHz) δ189.5, 178.0, 171.1, 138.5, 133.6, 133.1, 128.9, 128.6, 128.4, 127.9, 127.6, 104.5, 72.8, 55.6, 52.6, 44.6, 40.4, 36,7, 28.9, 28.8; IR (neat) $v_{max}$ 3500–2600 (br, CO$_2$H), 2974, 1738, 1717, 1691, 1542, 1443, 1351, 1256, 1231, 1165 cm$^{-1}$; FABHRMS (NBA) m/e 438.1550 ($C_{24}H_{23}NO_7$+H$^+$ requires 438.1553). Anal. Calcd for $C_{24}H_{23}NO_7$: C, 65.90; H, 5.30; N, 3.20. Found: C, 65.78; H, 5.19; N, 3.02.

EXAMPLE 4

(1R*,2S*,4R*,5S*,6S*)-6-Amino-6-benzoyl-5-phenylbicyclo[2.2.1]heptane-2-hemisuccinate (Compound 5)

A solution of Compound 12 (269 mg, 0.616 mmol) in CH$_3$OH (9 mL, 0.07M) was warmed at 45° C. The reaction solution was treated with Raney Ni (50 percent slurry in H$_2$O, 100 mg) and allowed to stir at 45° C. for 20 hours under a H$_2$ atmosphere. The Raney Ni was removed by filtration through Celite and washed successively with CH$_3$H (3×10 mL) and THF (3×10 mL). The combined organic phase was concentrated under pressure. Chromatography (SiO$_2$, 3×15 cm, 1–3 percent CH$_3$OH—CH$_2$Cl$_2$ gradient elution) afforded 4 as a white foam (74 mg, 250 mg theoretical, 30 percent): mp 78°–82° C. (CH$_2$Cl$_2$, white plates); $^1$H NMR (CDCl$_3$, 250 MHz) δ7.33 (d, 2H, J=7.4 Hz), 7.27–7.01 (m, 8H), 5.56 (d, 1H, J=6.2 Hz, C2-H), 5.05 (br s, 2H, NH$_2$), 2.93 (s, 1H, C5-H), 2.89 (s, 1H, C1-H), 2.66 (m, 4H), 2.44 (d, 1H, J=11.2 Hz, C7-H syn to ketone), 2.35 (d, 1H, J=3.2 Hz, C4-H), 2.22 (m, 1H, C3-H), 1.90 (d, 1H, J=11.1 Hz, C7-H anti to ketone), 1.73 (dd, 1H, J=13.7, 3.3 Hz, C3-H); $^{13}$C NMR (CDCl$_3$, 50 MHz) δ202.8, 177.3, 172.2, 142.0, 136.5, 131.1, 129.2, 128.8, 128.4, 127.6, 126.7, 74.1, 72.0, 64.0, 51.1, 45.1, 40.5, 36.0, 29.7, 29.4; IR (neat) $v_{max}$ 3509, 3500–2600 (br, CO$_2$H), 2962, 2924, 2854, 1722, 1684, 1263, 1231, 1165 cm$^{-1}$; FABHRMS (NBA) m/e 408.1813 ($C_{24}H_{25}NO_5$+H$^+$ requires 408.1811). Anal. Calcd for $C_{24}H_{25}NO_5$: C, 70.75; H, 6.18; N, 3.44. Found: C, 70.58; H, 6.41; N, 3.66.

The foregoing is intended as illustrative of the present invention but not limiting. Numerous variations and modifications can be effected without departing from the true spirit and scope of the invention.

What is claimed:

1. A process for carrying out a syn elimination to form a cis olefin that comprises the steps of:
   (a) admixing in an aqueous medium at a pH value of about 7 to about 10
      (i) an acyclic substrate ligand of the formula I to form a reaction mixture

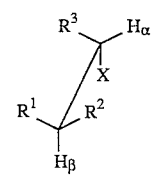

wherein $R^1$ is a substituent containing a five- or six-membered ring or a chain of atoms containing up to about 10 atoms in the chain that is long enough to fold to approximate the structure of a five- or six-membered ring;

$R^2$ is a substituent group other than hydrogen having a stearic bulk that is less than that of $R^1$, and the sum of the Hammett $\sigma_m$ values of $R^1$ and $R^2$ is about +0.3 to about +0.8;

$R^3$ is a substituent containing a five- or six-membered ring or a chain of atoms containing up to about 10 atoms in the chain that is long enough to fold to approximate the structure of a five- or six-membered ring, and has a Hammett $\sigma_p$ value of about zero or less;

X is a leaving group; and $H_\alpha$ and $H_\beta$ are hydrogens bonded to carbon atoms $\alpha$ and $\beta$ to X, respectively; and (ii) a catalytically effective amount of monoclonal antibodies or paratope-containing portions that bind to said substrate ligand and also bind to a bicyclic analogue ligand immunogen having the structure of formula III

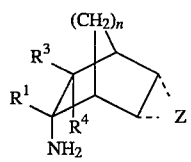

wherein (a) $R^1$ and $R^3$ are as defined above, $R^4$ is a hydrogen or a substituent of about the same size and shape as X, n is 1 or 2, and z is a carboxyl-terminated haptenic linking group for bonding the analogue ligand to an immunogenic carrier, Z being bonded to one or the other of the two carbons of a compound of formula III to which Z is linked by dotted lines; and (b) maintaining said reaction mixture under biological reaction conditions for a time period sufficient for said substrate ligand to be converted to a corresponding cis olefin of formula II

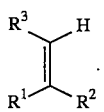

2. The process according to claim 1 wherein each of $R^1$ and $R^3$ contains a five- or six-membered ring.

3. The process according to claim 1 wherein $R^4$ is hydrogen.

4. A process for carrying out a syn elimination to form a cis olefin that comprises the steps of:

(a) admixing in an aqueous medium at a pH value of about 8 to about 9

(i) an acyclic substrate ligand of the formula I to form a reaction mixture

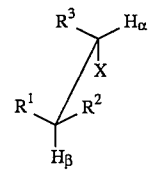

wherein $R^1$ is a substituent containing a five-or six-membered ring;

$R^2$ is a substituent group other than hydrogen having a stearic bulk that is less than that of $R^1$, and the sum of the Hammett $\sigma_m$ values of $R^1$ and $R^2$ is about +0.4 to about +0.7;

$R^3$ is a substituent containing a five- or six-membered ring and has a Hammett $\sigma_p$ value of about zero or less;

X is a leaving group; and $H_\alpha$ and $H_\beta$ are hydrogens bonded to carbon atoms $\alpha$ and $\beta$ to X, respectively; and (ii) a catalytically effective amount of monoclonal antibodies or paratope-containing portions that bind to said substrate ligand and also bind to a bicyclic analogue ligand immunogen having the structure of formula III

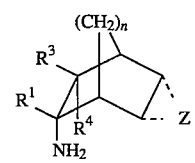

wherein (a) $R^1$ and $R^3$ are as defined above, $R^4$ is a hydrogen or a substituent of about the same size and shape as X, n is 1 or 2, and Z is a carboxyl-terminated haptenic linking group for bonding the analogue ligand to an immunogenic carrier, Z being bonded to one or the other of the two carbons of a compound of formula III to which Z is linked by dotted lines; and (b) maintaining said reaction mixture under biological reaction conditions for a time period sufficient for said substrate ligand to be converted to a corresponding cis olefin of formula II

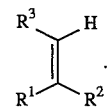

5. The process according to claim 4 wherein the substrate ligand has the formula

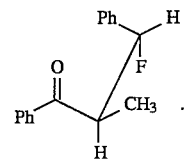

6. The process according to claim 5 wherein said bicyclic analogue ligand immunogen has the formula

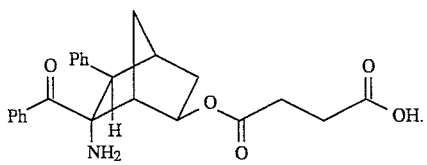

7. Hybridoma cells that secrete catalytic monoclonal antibody molecules that immunoreact with:
(i) an acyclic substrate ligand of the formula I

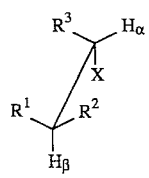

wherein $R^1$ is a substituent containing a five-or six-membered ring or a chain of atoms containing up to about 10 atoms in the chain that is long enough to fold to approximate the structure of a five- or six-membered ring;
$R^2$ is a substituent group other than hydrogen having a stearic bulk that is less than that of $R^1$, and the sum of the Hammett $\sigma_m$ values of $R^1$ and $R^2$ is about +0.3 to about +0.8;
$R^3$ is a substituent containing a five- or six-membered ring or a chain containing up to about 10 atoms in the chain that is long enough to fold to approximate the structure of a five- or six-membered ring, and has a Hammett $\sigma_p$ value of about zero or less;
X is a leaving group; and
$H_\alpha$ and $H_\beta$ are hydrogens bonded to carbon atoms $\alpha$ and $\beta$ to X, respectively; and
(ii) a bicyclic analogue ligand having the structure of formula III

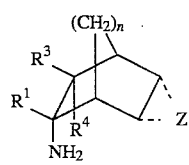

wherein
(a) $R^1$ and $R^3$ are as defined above,
$R^4$ is a hydrogen or a substituent of about the same size and shape as X,
n is 1 or 2, and
Z is a carboxyl-terminated haptenic linking group for bonding the analogue ligand to an immunogenic carrier, Z being bonded to one or the other of the two carbons of a compound of formula III to which Z is linked by dotted lines;
the paratopic portions of said monoclonal antibodies catalyzing a syn elimination reaction in said substrate to form a cis olefin of formula II

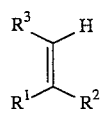

when admixed therewith in an aqueous medium at a pH value of about 7 to about 10.

8. The hybridoma according to claim 7 wherein $R^1$ and $R^3$ each contain a five- or six-membered ring.

9. The hybridoma according to claim 8 wherein $R^4$ is hydrogen.

10. The hybridoma according to claim 7 wherein the substrate ligand corresponds to the formula

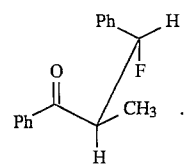

11. The hybridoma according to claim 10 wherein said analogue ligand has a structure corresponding to the formula

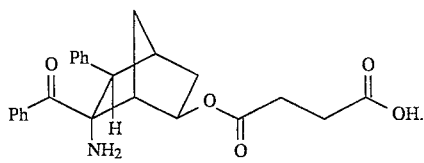

12. The catalytic monoclonal antibodies secreted by a hybridoma according to claim 7.

13. The catalytic monoclonal antibodies or paratopic portions secreted by a hybridoma according to claim 11 that is hybridoma ID4 having ATCC accession number HB 11704.

14. A process for using cyclohexadiene or cyclopentadiene to form a hapten containing eclipsed substituent groups useful for inducing production of paratopic molecules that catalyze the syn elimination of an acyclic substrate ligand of formula I

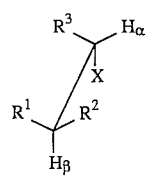

wherein $R^1$ is a substituent containing a five- or six-membered ring or a chain of atoms long enough to fold to approximate the structure of a five- or six-membered ring;
$R^2$ is a substituent group other than hydrogen having a steric bulk that is less than that of $R^1$; and
the sum of the Hammett $\sigma_m$ values of $R^1$ and $R^2$ is about +0.3 to about +0.8;
$R^3$ is a substituent containing a five- or six-membered ring or a chain of atoms long enough to fold to approximate the structure of a five- or six-membered ring, and has a Hammett $\sigma_p$ value of about zero or less;
X is a leaving group; and
$H_\alpha$ and $H_\beta$ are hydrogens bonded to carbon atoms $\alpha$ and $\beta$ to X, respectively comprising the steps of:

(a) reacting cyclopentadiene or cyclohexadiene in a Diels-Alder reaction with a cis nitroolefin of formula IV

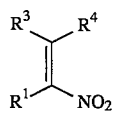   IV wherein
R$^1$ and R$^3$ are as defined above; and
R$^4$ is a hydrogen or a substituent of about the same size as X, to form a compound of formula V

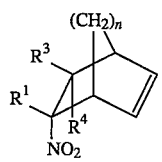   V (b) reducing the ethylenic double bond of a compound of formula V with a borane reductant and oxidizing the product of that reduction to form an alcohol of formula VI

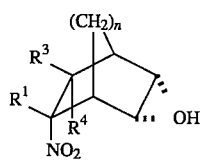   VI wherein the depicted hydroxyl group is bonded to one or the other of the two carbons of formula VI to which it is linked by dotted lines;
(c) reacting an alcohol of formula VI with a diacid or diacid precursor to form a compound of formula VII

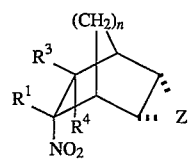   VII wherein Z is a carboxyl-terminated haptenic linking group, and is bonded to one or the other of the two carbon atoms of a compound of formula VII to which Z is linked by dotted lines;
(d) reducing the nitro group of a compound of formula VII to form the corresponding amine compound of formula III; and

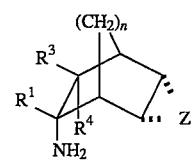   III recovering the compound of formula III.
15. The process of claim 14 wherein cyclopentadiene is utilized in said Diels-Alder reaction.
16. The process of claim 15 wherein each of R$^1$ and R$^3$ contains a five- or six-membered ring.
17. The process of claim 15 wherein R$^4$ is hydrogen.
18. The process of claim 15 wherein the compound of formula III has the structure

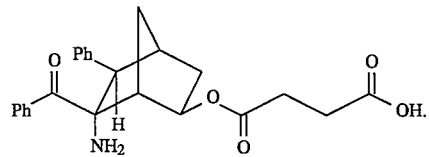

* * * * *